United States Patent [19]
Dimeff

[11] 3,938,956
[45] Feb. 17, 1976

[54] MODULATED HYDROGEN ION FLAME DETECTOR

[75] Inventor: John Dimeff, San Jose, Calif.

[73] Assignee: The United States of America as represented by the National Aeronautics and Space Administration Office of General Counsel-Code GP, Washington, D.C.

[22] Filed: June 28, 1974

[21] Appl. No.: 484,209

[52] U.S. Cl............................................. 23/254 EF
[51] Int. Cl.².......................................... G01N 27/62
[58] Field of Search......... 324/33, 77 G; 23/254 EF; 73/23.1, 25; 356/87; 55/67, 197

[56] References Cited
UNITED STATES PATENTS

| | | | |
|---|---|---|---|
| 3,443,415 | 5/1969 | Clardy | 73/23.1 |
| 3,740,154 | 6/1973 | Green | 356/87 |

OTHER PUBLICATIONS

George, S.F. "Effectiveness of Crosscorrelation Detectors" Proc. of National Electronics Conf., Vol X, Feb. 8 1955.

Primary Examiner—Alfred E. Smith
Assistant Examiner—Wm. H. Punter
Attorney, Agent, or Firm—Darrell G. Brekke; Armand G. Morin, Sr.; John R. Manning

[57] ABSTRACT

In a hydrogen flame detector there is provided a means for modulating the density of a gas stream prior to its introduction into the detector flame. A detector, responsive to the resulting modulation of the flame, is provided for producing an output signal having a component fluctuating at the frequency of modulation. A cross-correlator, responsive to the output signal and a signal at the frequency of modulation, is provided for producing a resultant signal proportional to the cross-correlation between its two input signals. A means is further provided for recording or otherwise utilizing the resultant signal thus produced.

4 Claims, 2 Drawing Figures

MODULATED HYDROGEN ION FLAME DETECTOR

The invention described herein was made by an employee of the United States Government and may be manufactured and used by or for the Government for governmental purposes without the payment of any royalties thereon or therefor.

BACKGROUND OF THE INVENTION

The purpose of the invention is to provide an improved apparatus for and method of detecting ions in a hydrogen flame detector. The hydrogen flame detector is an analytical instrument typically used for chemical analysis at the output port of an instrument such as a gas chromatograph. In the instrument, hydrogen is burned in the vicinity of two electrodes. An unknown chemical introduced into the flame is ionized, thereby causing the flow of a small ionic current between the electrodes. As the quantity or the composition of the unknown chemical changes, a variation in this ionic current is detected and correlated with the chemical changes.

The ionic currents are measured by any of a number of electrometer-type devices. The measurement precision of each of these devices, however, is limited by several physical factors. Photoemission, thermoelectric effects, instabilities in flame temperature, and other effects, for example, cause instabilities which mask small variations introduced by the chemicals under test. These limiting factors are overcome by the invention described herein.

SUMMARY OF THE INVENTION

In view of the foregoing, two principal objects of the present invention are an apparatus for and a method of overcoming the aforementiond limiting factors of prior known hydrogen flame detectors.

Consistent with these objects, a principal feature of the present invention involves modulating the density of an unknown chemical prior to its introduction into the hydrogen flame. This modulation is accomplished by mechanically changing the flow impedance in the tubes through which the chemical is introduced, by aerodynamically modulating the density of the stream carrying that sample, as by a fluidic oscillator, or by a periodically displaced piston, for example, or by other appropriate means. The periodic variation in density of the unknown chemical will introduce a variation of similar period in the ion current passing between the two sensing electrodes. A signal derived from the device modulating the density of the unknown chemical is shifted in phase and multiplied by the output of the ion current detecting circuit to provide a large resultant signal which is proportional to the cross-correlation between the two signals. Since the modulation period can be readily adjusted to values that are very small compared to the periods which characterize the unwanted photoionic, photoelectric, etc. drifts, the cross-correlation between the signals due to these unwanted effects and the modulation signal will be extremely small and random.

The device thereby improves the ability of the hydrogen flame detector to discriminate the desired signal by reducing its sensitivity to undersired error signal.

DESCRIPTION OF THE DRAWING

The above and other objects, features and advantages of the present invention will become apparent to those skilled in the art upon a reading of the following detailed description of preferred embodiments thereof as shown in the accompanying drawings in which.

DETAILED DESCRIPTION

Figure 1:
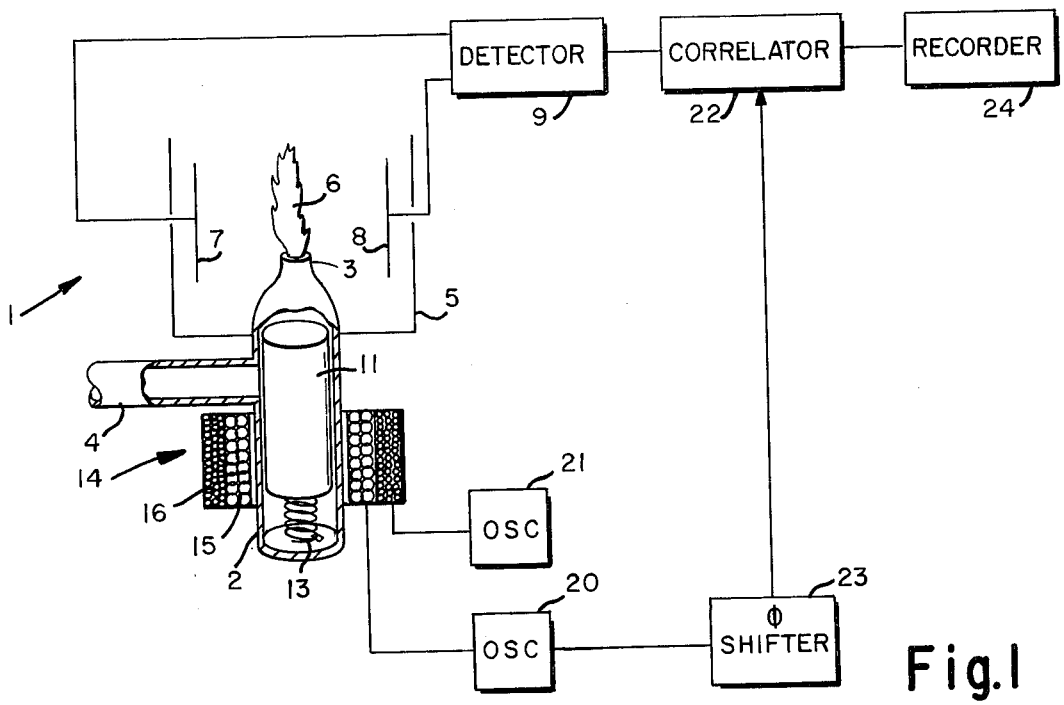
FIG. 1 is a diagrammatic and block diagram of a single-flame embodiment of the present invention.

Referring to FIG. 1, there is provided, in accordance with the present invention, a single-flame embodiment of a hydrogen flame detector, designated generally as 1. In this embodiment, detector 1 comprises a main gas chamber 2. Chamber 2 is terminated at one end by a gas nozzle 3. In gas communication with and extending from chamber 2 there is provided a gas inlet, port or tube 4. Tube 4 is provided for inputing a mixture of hydrogen and an unknown gas prepared by conventional methods and apparatus (not shown) into chamber 2. Extending outwardly from and generally surrounding nozzle 3 is a burner or combustion chamber 5 for enclosing a flame 6 of said mixture issuing from nozzle 3. Interior to chamber 5 is a pair of electrodes 7 and 8. Electrodes 7 and 8 are generally situated on opposite sides and spaced from nozzle 3 and electrically coupled to a detector 9 which includes a conventional source of bias potential for collecting ions created in the flame 6.

The particular bias used in a given instance will, of course, depend on the electronic means used for detection. Consequently the source of bias may be any of several conventional means for providing bias, such as, for example, a carrier voltage for detecting capacitance changes, a d.c. bias to collect ions, or a current source for measuring resistance changes induced by the flame 6 extending between the electrodes 7 and 8.

It will be recognized that the apparatus of the present invention as described thus far is typically found in conventional hydrogen flame detectors and accordingly, without more, would provide a measurement precision limited, for example, by the several physical factors of photoemission, thermoelectric effects and instabilities in flame temperature as previously discussed.

To improve the ability of a detector to discriminate the desired signal by reducing its sensitivity to undesired error signals, there is additionally provided in chamber 2, a permanent magnet 11. Magnet 11 is supported in chamber 2 on a spring 13. Surrounding chamber 2, magnet 11 and spring 13, there is provided an external coil 14. Coil 14 is wound in a conventional manner so as to include a high current segment 15 for forcibly deflecting magnet 11 at the natural resonant frequency determined by the magnet 11 and the spring 13 and a high impedance section 16 which is wound in a conventional manner so as to allow the use of a carrier signal in a standard arrangement for detecting the position of the magnet 11 in the chamber 2. For the latter purpose, the frequency of the carrier signal is typically much higher than the aforementioned mechanical resonant frequency of the magnet 11 and the spring 13.

The driving and position detection signals for magnet 11 are provided by a pair of oscillators 20 and 21, which are coupled to their respective segments 15 and 16 of the coil 14. The oscillator 20 outputs an adjustable relatively low-frequency signal for driving the magnet 11 — e.g., 3–300 $H_z$. The oscillator 21 outputs a relatively high-frequency signal for detecting the position of magnet 11 and, in detecting the position of magnet 11, provides a control signal to oscillator 20 so as to drive magnet 11 at a constant amplitude at the resonant frequency of the magnet 11 and the spring 13.

As will be appreciated, the periodic oscillation of magnet 11 effects a modulation of the density of the gas mixture burning at nozzle 3 and hence produces a corresponding periodicity in the flame characteristics — specifically, the ionic current in the flame, as measured by the electrodes 7 and 8. This periodicity ultimately appears as a component in the output of detector 9 which fluctuates at the frequency of modulation of the magnet 11.

To measure this component and discriminate from signal components fluctuating at other frequencies in the output of the detector 9, the output of detector 9 is coupled to one input of a correlator 22. To provide a reference signal for correlator 22, there is coupled to a second input of the correlator 22, a phase shifter 23. The input of shifter 23 receives its input from the oscillator 20 for providing a reference signal for correlator 22 which corresponds to the quotient of the volume of gas modulated within the chamber 2 and the rate of flow of the modulated gas from the chamber 2. In correlator 22, in a conventional manner, the output signal of the detector 9 and the reference signal from the shifter 23 are multiplied for providing a large resultant signal which is proportional to the cross-correlation between the two signals. The resultant signal is then available for display or recording on a recorder 24 or for any other suitable utilization, as, for example, integration or the like.

Figure 2:
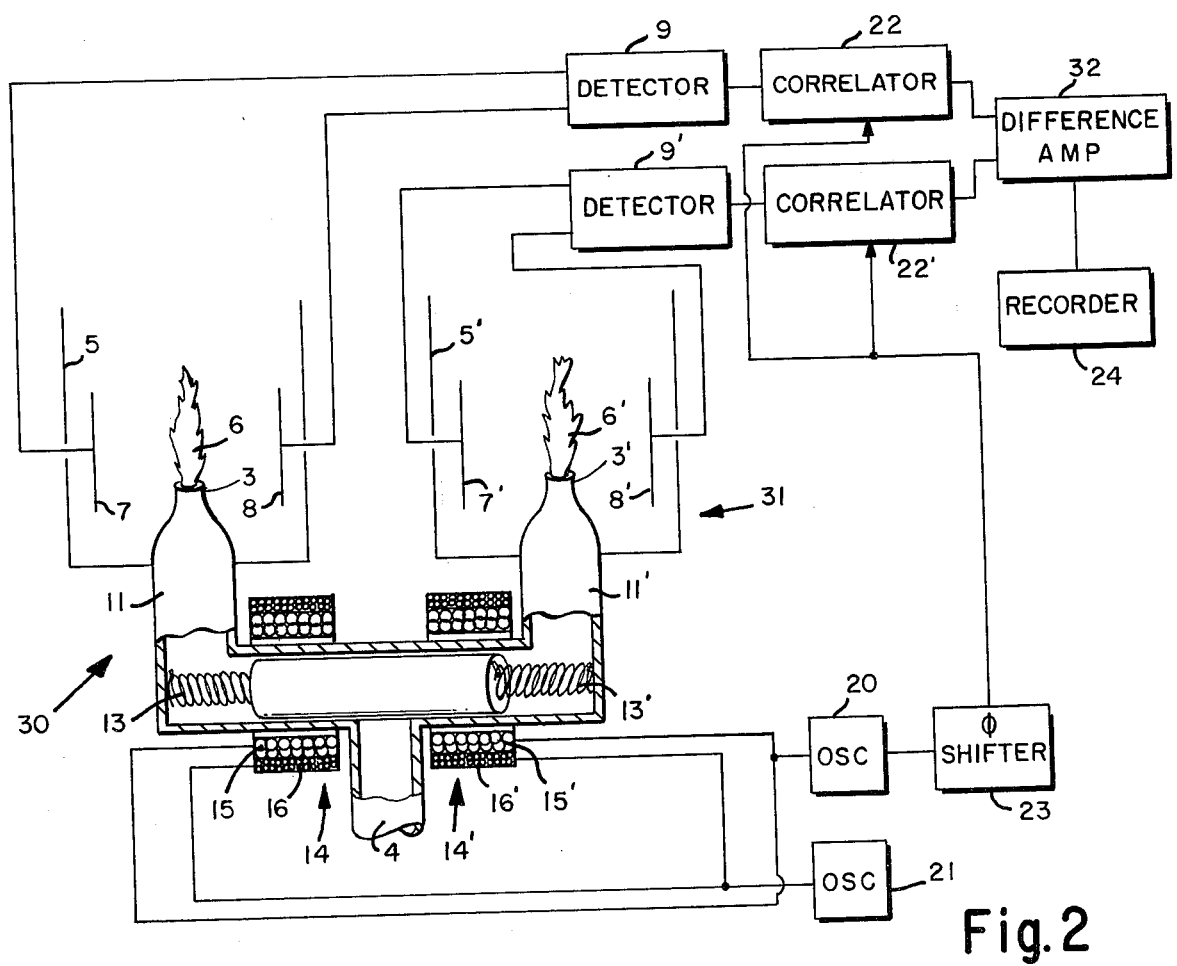
FIG. 2 is a diagrammatic and block diagram of a dual-flame embodiment of the present invention.

Referring to FIG. 2, there is provided an alternative embodiment of the present invention comprising a dual-flame hydrogen flame detector in which a gas stream from an input port or tube 4 is branched into two substantially identical sections, designated generally as 30 and 31. Those component parts of each of sections 30 and 31, which are the same structurally and functionally as the parts of FIG. 1, retain the designations used in FIG. 1. Those parts which are duplicates of the parts of FIG. 1 are identified by the designations used in FIG. 1, but with primes. The only significant structural difference between the embodiments of FIGS. 1 and 2, aside from the duplication of component parts, is that the magnet 11 is coupled at both ends to a spring 13 and 13' for modulating the gas prior to its introduction into the flames 6 and 6'.

Consequently, the right and left sections 30 and 31 operate in phase opposition. Because of this functional difference, there is additionally provided, coupled between the outputs of correlators 22 and 22' and the input of the recorder 24, a difference amplifier 32 for providing a signal to the recorder 24 corresponding to the difference between the signals derived from the two out-of-phase detectors 9 and 9'.

In light of the foregoing description, it will be apparent to those skilled in the art that various modifications may be made within the spirit and scope of the invention. The means illustrated for modulating the gas and, hence, the flame can be replaced, for example, by a simple acoustical driver, such as a speaker, a rotating mechanical valve, a fluidic "flip-flop" or oscillator, or any of a number of other devices without changing the inherent operation of the system. Moreover, various mixtures of gas and other chemicals as well may be analyzed by means of the method and apparatus of the present invention. Accordingly, it is understood that the scope of the present invention is to be restricted only to the extent of the claims as hereinafter provided.

What is claimed is:

1. In a hydrogen flame detector having a means forming a chamber for receiving a mixture of a known gas and an unknown gas; a means forming a nozzle at one end of said chamber for providing a flame of said mixture of gases; and an electrode means for collecting ions of said unknown gas generated in said flame, the improvement comprising:
   a means for modulating the density of said mixture of gases in said chamber at a predetermined frequency prior to their introduction into said flame, said modulation of said mixture serving to modulate said ions of said unknown gas at said predetermind frequency;
   a means coupled to said electrode means for providing an output signal in response to said modulated ions having a component fluctuating at said predetermined frequency;
   a means responsive to said modulating means for generating a reference signal having a component fluctuating at said predetermined frequency;
   a means responsive to said output and said reference signals for providing a resultant signal corresponding to the cross-correlation between said first and said second output signal; and
   a means coupled to said resultant signal generating means for utilizing said resultant signal.

2. A hydrogen flame detector according to claim 1 wherein said modulating means comprises:
   a movable means positioned within said chamber;
   a means generating a modulation signal for moving said movable means at said predetermined frequency; and further wherein said reference signal generating means comprises means responsive to said modulation signal generating means for phase shifting said modulation signal by an amount proportional to the quotient of the volume of said gases being modulated and their rate of flow from said chamber for generating said reference signal.

3. A hydrogen flame detector according to claim 2 wherein said movable means comprises a permanent magnet piston and said means for generating said modulation signal includes means for oscillating said piston at a constant amplitude and at said predetermined frequency.

4. A hydrogen flame detector according to claim 3 wherein said predetermined frequency is in the range of 3 to 300 $H_z$.

* * * * *